United States Patent [19]

Rhoda

[11] 4,335,087

[45] * Jun. 15, 1982

[54] PROCESS FOR PREPARING CIS-Pt(NH$_3$)$_2$Cl$_2$

[75] Inventor: Richard N. Rhoda, Suffern, N.Y.

[73] Assignee: MPD Technology Corporation, Wyckoff, N.J.

[*] Notice: The portion of the term of this patent subsequent to Jun. 16, 1998, has been disclaimed.

[21] Appl. No.: 206,883

[22] Filed: Nov. 14, 1980

Related U.S. Application Data

[62] Division of Ser. No. 65,553, Aug. 16, 1979, Pat. No. 4,273,755.

[51] Int. Cl.$^3$ .............................................. C01G 55/00
[52] U.S. Cl. .................................. 423/413; 423/397
[58] Field of Search ............... 423/413, 463, 22, 397; 424/131

[56] References Cited

U.S. PATENT DOCUMENTS

| | | | |
|---|---|---|---|
| 4,053,587 | 10/1977 | Davidson | 424/131 |
| 4,075,307 | 2/1978 | Kerr et al. | 423/413 |
| 4,079,121 | 3/1978 | Kerr | 423/413 |
| 4,273,755 | 6/1981 | Rhoda et al. | 423/463 |

FOREIGN PATENT DOCUMENTS 472342  3/1979  Spain .

OTHER PUBLICATIONS

Keller, R., "Potassium Tetrachloroplatinate (II)" *Inorganic Syntheses* II, pp. 247–253 (1946).
Speer, R., "Coordination Complexes of Platinum as Antitumor Agents" *Cancer Chemotherapy Reports*, Part 1, 59(3), pp. 629, 630 (1975).
Dhara, S. C., "A Rapid Method for the Synthesis of cis-[Pt(NH$_3$)$_2$Cl$_2$]", *Indian J. Chem.* 8, 193–194 (1970).
Kauffman, G., "cis- And trans-Dichlorodiammine Platinum II", Inorganic Syntheses VII, pp. 239–245 (1963).
Gildengershel, *Zhurnal Neorganicheskoi Khimii*, vol. 1 (1956), pp. 1745–1749.
King, "Researches on Amines Part IX", *Journal Chem. Soc.*, Pt. 2 (1938), pp. 1338–1346.
C. Lock et al., "The Structure of Platinum Anticancer Agents and Their Metabolites", *J. Clin. Hematol. Oncol.*, 7(1), pp. 63–78 (1977).
Chem. Abst., vol. 86, No. 24, 182241k (1977).

*Primary Examiner*—Brian E. Hearn
*Attorney, Agent, or Firm*—Raymond J. Kenny; Miriam W. Leff

[57] ABSTRACT

A process is provided for preparing cis-Pt(NH$_3$)$_2$Cl$_2$ and intermediates. The cis-Pt(NH$_3$)$_2$Cl$_2$ is provided in high yield and purity.

4 Claims, No Drawings

PROCESS FOR PREPARING CIS-Pt(NH$_3$)$_2$Cl$_2$

This is a division, of application Ser. No. 65,553, filed Aug. 16, 1979, now U.S. Pat. No. 4,273,755.

The present invention relates to the preparation of cis-platinum(II) complexes. More specifically it concerns improved methods of preparing cis-diamminedichloroplatinum(II) and intermediate compounds used in such preparation.

Cis-diamminedichloroplatinum(II) is not a new compound. It was first reported in 1844 and named Peyrone's chloride after its inventor. Recently, this compound has been of particular interest because it has been found to have anti-cancer activity. When used as an anti-cancer agent the compound must be exceedingly pure. Specifications set up by the National Cancer Institute (NCI) require that to be acceptable the salt should contain no more than 1% of the trans-isomer. There is also evidence that the presence of any ionic species, e.g. Magnus' green salt and silver, in the final product should be as low as possible. Because platinum is so expensive, the yields should be high, otherwise the process would not be commercially acceptable. Several syntheses are known but all give unacceptable quantities of both the trans-isomer and the double Magnus' green salt, [Pt(NH$_3$)$_4$] [PtCl$_4$] as co-precipitates. A few companies are presently preparing cis-Pt(II) salts of acceptable purity but the methods used are proprietary.

R. J. Speer et al. in "Cancer Chemotherapy Reports" Part I 59 (3), May/June 1975 indicate that cis-diamminedichloroplatinum(II) is rather toxic and that it has a low therapeutic index that is very dependent on its purity. They also recommend alternative routes to the synthesis and purification of the compound. One method for synthesis is that suggested in the literature by Kauffman and Cowan and the other by Dhara. The purification technique recommended is rather sparse in details, and details are lacking in conditions used in the various steps in the alternative methods for synthesis. The present method is an improvement over the alternative methods with respect to specific steps and with respect to the overall method for producing cis-Pt(NH$_3$)$_2$Cl$_2$.

INVENTION

In accordance with the present invention a cis-diamminediiodoplatinum(II) complex, cis-Pt(NH$_3$)$_2$I$_2$, of high purity and in high yield is prepared from potassium tetraiodoplatinum(II) salt by a method comprising: adding an aqueous solution of ammonium hydroxide to an aqueous dispersion of potassium tetraiodoplatinum(II), said tetraiodo salt having the formula K$_2$PtI$_4$, under a controlled gradually rising temperature profile, preferably stepwise between about 40° C. and about 60° C., while controlling the ammonium hydroxide addition so that the pH does not exceed 7.5, and preferably the pH does not exceed 7. The addition of NH$_4$OH is controlled by slow addition, stirring the mixture vigorously during the addition, and monitoring the pH during the addition. Under these conditions, yields of at least about 91% cis-Pt(NH$_3$)$_2$I$_2$ can be obtained, and typically yields of 91–97%. Using this technique as a step in a route in preparing cis-Pt(NH$_3$)$_2$Cl$_2$ as the product, the crude product can be obtained with little or no Magnus' green salt and less than 1% of the transisomer.

As a further aspect of the invention cis-diamminediaquaplatinum(II) nitrate (i.e. cis-[Pt(NH$_3$)$_2$(H$_2$O)$_2$](NO$_3$)$_2$) is prepared from a cis-diamminediiodoplatinum(II) salt by a method comprising slowly adding the cis-diamminediiodoplatinum(II) to an aqueous solution of silver nitrate at room temperature and with rapid stirring and then warming the solution to no higher than about 50° C. The conversion for this method is essentially quantitative.

To produce the cis-diaqua salt with minimum silver ion in solution, the amount of AgNO$_3$ used is monitored carefully. For example, the AgNO$_3$ may be used slightly under stoichiometric amount. After separation of the silver iodide precipitate, a small amount (e.g., 0.5 gram relative to 200 g of product in 2500 ml solution) of solid KCl (or NaCl) is stirred into the filtrate to precipitate residual Ag$^+$ and the resultant product is filtered to remove any precipitate. Alternatively, avoidance of unreacted Ag$^+$ in solution can be effected by using a Ag/AgCl electrode.

In still another aspect of the present invention cis-diamminedichloroplatinum(II) is produced in high purity and in high yield from cis-diamminediaquaplatinum(II) nitrate by a method comprising rapidly adding solid MCl (M=, e.g. K, Na) to a solution of cis-diamminediaquaplatinum(II) nitrate at room temperature, warming the mixture to a temperature of about 65° C. to 75° C., e.g., 70° C., and holding it at temperature to allow completion of the reaction permitting the resultant product to cool to a temperature no lower than about 10° C., to about 15° C. and preferably to room temperature, and then, without permitting the product to stand, separating the precipitate from the solution.

By using the combined preparation steps given above for preparing the cis-diamminedichloroplatinum(II) from the tetraiodoplatinum(II) salt high yields of the crude product can be obtained with substantially no Magnus' green salt and less than 1% trans-isomer.

The crude cis-diamminedichloroplatinum(II) can be purified by one or more recrystallizations from 0.1 N HCl by adding to the dilute hydrochloric acid solution, heating to 100° C., filtering hot and permitting the solution to cool to room temperature and/or by recrystallization at room temperature from N,N'-dimethylformamide (DMF) with 0.1 N HCl addition.

In accordance with another aspect of the present invention the tetrachloro salt of platinum(II) is produced in improved yield from K$_2$PtCl$_6$ with hydrazine dihydrochloride by mixing aqueous solutions of the reactants at substantially room temperature.

To insure high purity of the end product, the synthesis must be made with very high purity elemental platinum as the initial material and very high purity reagents. Highly pure chloroplatinic acid is commercially available. If desired, elemental platinum can be converted to chloroplatinum acid, e.g. with aqua regia, using methods known in the art.

Chloroplatinic acid can be converted to the insoluble K$_2$PtCl$_6$ by treatment with potassium chloride. The conversion can be to the sodium salt with NaCl, but potassium is preferred for obtaining a higher yield. The reaction proceeds in an aqueous medium typically at a temperature in the range of about 55° to 60° C., preferably about 55° C. When cooled to 0° C. a very good yield of the platinum salt can be obtained. No alcohol is necessary.

DESCRIPTION OF PREFERRED EMBODIMENTS

It will be appreciated that tetrachloro and hexachloro salts of platinum(II) and (IV) such as $K_2PtCl_4$ and $K_2PtCl_6$ are commercially available and that each of the improved steps of the present invention can be carried out at any stage in the synthesis. The following description of the present process, however, will show a preferred embodiment of the present invention starting with high purity chloroplatinic acid and obtaining material which will meet National Cancer Institute (NCI) specification of Dec. 9, 1975 for compound No. NSC-119,875 (cis-Pt[$NH_3$]$_2Cl_2$). In the following description and the examples which follow: All reactions are carried out using a magnetic stirrer. All materials used are very pure. Room temperature means about 25° C. Yields were determined by wet chemical analysis initially and thereafter gravimetrically, except if otherwise indicated.

STEP 1

Reaction: $H_2PtCl_6 + 2KCl \rightarrow K_2PtCl_6 + 2HCl$

An aqueous solution containing roughly 0.25 moles per liter of chloroplatinic acid heated to about 55° C.±5° C. is treated by slow, dropwise addition of a concentrated aqueous solution of KCl. The amount of KCl used is stoichiometric for complete conversion to $K_2PtCl_6$ which forms as a yellow precipitate. The reaction mixture need not be heated. However, it is preferred to elevate the temperature moderately, e.g. to about 50° C., to ensure that the reaction goes to completion and that no KCl gets entrapped in the $K_2PtCl_6$. Also, to ensure complete conversion a very slight excess of KCl can be added. The product is cooled to 0° C. and permitted to stand, e.g. overnight, to ensure complete precipitation.

After filtration, the residue is washed with cold distilled water, e.g., with three 500 ml portions of water, and then with absolute ethyl alcohol, e.g., with a 500 ml portion of alcohol. The washed residue is dried, e.g., for 2 hours at 110° C. The filtrate is kept for platinum recovery. A yield of 95% has been obtained.

STEP 2

Reaction:
$2K_2PtCl_6 + N_2H_4 \cdot 2HCl \rightarrow 2K_2PtCl_4 + N_2\uparrow + 6HCl$ The dried $K_2PtCl_6$ (about 0.5 mole) is dispersed in 2000 ml of distilled water and an aqueous solution of $N_2H_4 \cdot 2HCl$ containing a 5% excess of stoichiometric amount, is added dropwise with vigorous stirring. The addition is done at room temperature and the flow of reagent is adjusted so that addition takes 30 minutes. Thereafter the resultant mixture is warmed to 50°–60° C. until the yellow precipitate disappears. This takes typically one hour. Thereafter the resultant red solution is heated to 85° C. and held there for 15 minutes, then cooled to room temperature and refrigerated overnight. Essentially complete conversion to the tetrachloride can be achieved without decomposition to elemental Pt.

To ensure the removal of any unreacted $K_2PtCl_6$, the product of Step 2 is cooled to about 0° C. and permitted to stand. For convenience the product may be refrigerated overnight. In carrying out Step 2 care should be taken to add sufficient hydrazine to react with the $K_2PtCl_6$, only slight excess, e.g. 5% is used, since with too great an excess of hydrazine causes reduction to Pt°. The vessel used for the reaction should be free from cracks or scratches which may serve as sites for nucleation of Pt°.

STEP 3

Reaction: $K_2PtCl_4 + 4KI \rightarrow K_2PtI_4 + 4HCl$

The potassium tetrachloroplatinum(II) solution is warmed to 40° C. and an aqueous solution of 10 molar KI is added dropwise in sufficient amount for complete conversion to the tetraiodo salt. A black precipitate of $K_2PtI_4$ begins to form. Typically this takes place 1 hour, after which the solution is heated to 85° C. and held there for 15 minutes. Essentially complete conversion can be achieved. The product is cooled to at least 40° C. for use in the next step.

STEP 4

Reaction: $K_2PtI_4 + 2NH_4OH \rightarrow cis\text{-}Pt(NH_3)_2I_2 + 2KI + 2H_2O$ To the $K_2PtI_4$ containing solution of Step 3 at 40° C., a diluted solution of $NH_4OH$ is added dropwise using a pH meter so that pH 7 is not exceeded during the addition. $K_2PtI_4$ has a pH of about 4.9 in water at room temperature. However, sufficient $NH_4OH$ must be added to neutralize the HCl in solution as well as to react with the $K_2PtI_4$. (If the $K_2PtI_4$ is used as a water dispersion the reaction would only require sufficient $NH_4OH$ to react with the $K_2PtI_4$, using proper precautions with regard to pH, temperature and the manner in which the $NH_4OH$ is added.) The dilute $NH_4OH$ is added until the black precipitate disappears, typically 3 to 4 hours. The solution is warmed to 60° C. for 1 hour, adding dilute $NH_4OH$ as needed to pH=7, and then the reaction mixture is cooled to room temperature. A dark greenish brown precipitate forms which is filtered. The resultant precipitate is washed with distilled water and then absolute ethyl alcohol, e.g., three washes with 500 ml water and one with 500 ml alcohol. The filtrate is kept for platinum recovery. The yield is typically about 91% for Steps 2, 3 and 4, but a yield as high as 97% has been obtained.

STEP 5

Reaction: $cis\text{-}Pt(NH_3)_2I_2 + 2AgNO_3 + 2H_2O \rightarrow cis\text{-}[Pt(NH_3)_2(H_2O)_2](NO_3)_2 + 2AgI$ After dissolving $AgNO_3$ in distilled water, solid cis-$Pt(NH_3)_2I_2$ is added slowly to the solution at room temperature with rapid stirring. Typically addition of the cis-diamminediiodoplatinum(II) to the solution of $AgNO_3$ takes about 30 minutes, and the resultant mixture is stirred for an additional period of time, e.g., about 10 minutes, and then it is warmed to 50° C. and held there for a short period of time, e.g., 15 minutes, to ensure complete reaction. Thereafter the reaction mixture is cooled to room temperature and filtered to remove the AgI precipitate.

The AgI precipitate is washed, e.g., with three 500 ml portions of hot distilled water.

When it is particularly desirable to minimize the silver level in the product, the $AgNO_3$ reagent is used slightly below the stoichiometric amount. To the separated filtrate after reaction with $AgNO_3$, a small amount of solid KCl, e.g. 0.5 g KCl, is added and after stirring at room temperature for a short period, the product is filtered. Filtration can be carried out through the AgI precipitate and the residue can be kept for recovery of Ag.

The yield of the cis-diaqua salt in solution is quantitative. The high yields are insured by adding the cis-diamminediiodoplatinum(II) to the AgNO$_3$ solution. At room temperature the KCl serves to precipitate Ag$^+$ in solution. When the AgNO$_3$ is added, for example, to a hot solution of the iodo salt, as recommended in the art, the yields are not as high. In addition if reaction temperature is permitted to go above 50° C., e.g. to 65° C., then yields are not as high.

STEP 6

Reaction: cis-[Pt(NH$_3$)$_2$(H$_2$O)$_2$](NO$_3$)$_2$+2KCl→cis-Pt(NH$_3$)$_2$Cl$_2$+2KNO$_3$+2H$_2$O To the filtrate of Step 5 at room temperature and with stirring is added solid KCl in an amount of 10% excess, as quickly as possible. The mixture is warmed to 70° C. and held there for completion of the reaction, typically 1 hour, and the product allowed to cool to room temperature while stirring to avoid temperature gradient. As soon as the product is at room temperature, it is filtered and the residue washed. Washing is carried out with three 500 ml portions of distilled water followed by one 500 ml portion of absolute ethyl alcohol.

Co-precipitation of impurities can be avoided by cooling only to room temperature. Further cooling below room temperature, e.g., to 0° C. resulted in the appearance of traces of Magnus' green salt and other impurities in the final product.

A yield of 95% crude cis-Pt(NH$_3$)$_2$Cl$_2$ for Steps 6 and 7 has been obtained. The total yield from Steps 1 through 7 is typically 79%. All platinum can be recovered from discarded materials.

STEP 7

Reaction: Purification of Crude cis-Pt(NH$_3$)$_2$Cl$_2$ (a) First Recrystallization The crude product is added to 0.1 N NCl (about 1 g product to 35 ml 0.1 N HCl), and the solution is warmed to 100° C., filtered hot and then the filtrate is cooled to room temperature for recrystallizaton.

(b) Second Recrystallization

Repeat of first recrystallization step.

(c) Third Recrystallization

Before the third recrystallization step, a test for solubility according to the aforementioned NCI specification should be carried out. If the material does not pass the solubility test an alternative third recrystallization step is carried out as follows: The product of the second recrystallization step is dissolved in DMF. About 50 ml DMF/g of the cis-Pt product is sufficient. After filtration an equivalent volume of 0.1 N HCl is added with stirring and the mixture is permitted to stand with stirring for 20 minutes. The purified cis-Pt product precipitates and after filtration the residue is washed with absolute alcohol and vacuum dried.

It was found that the present product could be retained for a period of 3 days in 0.1 N HCl without any transformation to trans observed by paper chromatography test.

The above method is an improvement over known methods for producing cis-Pt(NH$_3$)$_2$Cl$_2$ in that it: gave (1) unexpectedly high yield of the desired product, (2) a pure cis-isomer free of Magnus' green salt and of the trans-isomer, and (3) a final compound with very low silver content.

For better understanding of the present invention by persons skilled in the art, some specific examples are given below by way of illustration.

EXAMPLE 1

Experiments were run essentially as described in Step 2 above, in which K$_2$PtCl$_6$ is reduced to K$_2$PtCl$_4$ using hydrazine, with the following variations:

| Exp. Type | Reagent | Initial Temperature | Pt Deposit (Pt°) Observed |
|---|---|---|---|
| A-1 | N$_2$H$_4$ . 2HCl | Room Temp. | None |
| B-1 | N$_2$H$_4$ | Room Temp. | Pt° immediately |
| C-1 | N$_2$H$_4$ . 2HCl | 50°–65° C. | Some Pt° on sides of beaker |

EXAMPLE 2

Experiments were run essentially as described in Step 4 above, in which K$_2$PtI$_4$ is converted to cis-Pt(NH$_3$)$_2$I$_2$ using NH$_4$OH, with the following variations:

| Exp. Type | Reagent | Condition | Yield cis-Pt(NH$_3$)$_2$I$_2$ |
|---|---|---|---|
| A-2 | NH$_4$OH | Temp. control gradual to 60° C. & gradual addition of NH$_4$OH & control pH not to exceed 7 | 96% |
| B-2 | NH$_4$OH | Stoichiometric NH$_4$OH added to solution at 60° C. & without pH control | 77% |

EXAMPLE 3

Experiments were carried out essentially as described in Step 5 above, in which cis-Pt(NH$_3$)$_2$I$_2$ in aqueous solution is converted with AgNO$_3$ to the cis-[Pt(NH$_3$)$_2$(H$_2$O)$_2$](NO$_3$)$_2$, with the following variations and results:

| Exp. Type | Variation Addition | Temperature | Yield* Crude |
|---|---|---|---|
| A-3 | cis-iodo salt added to AgNO$_3$ | Room Temp. | 95% |
| B-3 | cis-iodo salt added to AgNO$_3$ | 50° C. | 90% |
| C-3 | cis-iodo salt added to AgNO$_3$ | 90° C. | 78% |
| D-3 | AgNO$_3$ added to cis-iodo salt | Room Temp. | 84% |

*Since it is difficult to analyze for the diaqua compound, analysis was made for the yield of crude cis-Pt(NH$_3$)$_2$Cl$_2$ (i.e., the product obtained after carrying out step 6 on the filtrates obtained from the tests of this experiment).

EXAMPLE 4

Experiments were carried out essentially as described in Step 6 above, in which cis-[Pt(NH$_3$)$_2$(H$_2$O)$_2$](NO$_3$)$_2$ in solution is treated with KCl to form the crude cis-(Pt(NH$_3$)$_2$Cl$_2$, with the following variations and results:

| Exp. Type | Conditions | Yield | Observation Magnus' Salt |
|---|---|---|---|
| A-4 | 1 - Reaction at Room Temp. 2 - Warm to 70° C. 3 - Cool to 25° C. & Filter Immediately | 95% | None |
| B-4 | 1 - Reaction at Room Temp. 2 - Cool to 25° C. & Filter Immediately | 80% | None |
| C-4 | 1 - Reaction at Room Temp. 2 - Cool to 0° C. | — | Layer of Green Salt |

In another set of experiments three identical solutions containing cis-[Pt(NH$_3$)$_2$(H$_2$O)$_2$](NO$_3$)$_2$ were treated with KCl and the crude cis-platinum complex was permitted to form under the conditions of A-4 and after separation of the precipitate at 25° C., the filtrates were treated, respectively, under the three different conditions noted below, with the following observations:

| Exp. | Conditions | Observation |
| --- | --- | --- |
| D-4 | Filtrate No. 1 on cold plate Allowed to cool to 15° C. Allowed to cool to between 9–10° C. | More ppt of cis-Pt formed - no green salt Magnus' green salt came down |
| E-4 | Filtrate No. 2 stood at RT | Traces of Magnus' green salt in 3 hrs. |
| F-4 | Filtrate No. 3 stood at RT | Traces of Magnus' green salt in 3½ hrs. |

The tests showed the Magnus' green salt formed when the temperature fell below about 10° C. and when the reaction medium was permitted to stand at room temperature. Even though the Magnus' green salt did not form immediately, the tests show that it is advisable not to let the reaction medium stand at room temperature.

To maximize yield and ensure purity, the cis-Pt(NH$_3$)$_2$Cl$_2$ can be separated from solution in a stepwise fashion. For example, after cooling to room temperature the product is immediately filtered and the solution is permitted to stand until a further precipitation is formed. This is repeated until the formation of a green salt is observed.

EXAMPLE 5

Experiments were carried out essentially as described in Steps 3 and 4 above in which K$_2$PtCl$_4$ is converted to K$_2$PtI$_4$ using KI, and then K$_2$PtI$_4$ is converted to cis-Pt(NH$_3$)$_2$I$_2$ using a dilute solution of NH$_4$OH under pH control, with the following variations in pH control in Step 4 and results:

| Exp. | pH | % Yield(1) | Appearance of Product of Step 4 |
| --- | --- | --- | --- |
| A-5 | 7 | 91(2) | Dark greenish brown |
| B-5 | 7.5 | 88 | Dark brown |
| C-5 | 8 | 67 | Light brown |

(1)Yield based on Steps 3 and 4.
(2)Average yield based on 7 tests.

EXAMPLE 6

Samples were prepared using the method of the present invention essentially as described above in Steps 1 through 6 and then purified by recrystallization twice according to the 0.1 N HCl method of Step 7. Samples of the final product were screened according to the aforementioned NCI specification for the chemical NSC-119,875.

(A) In the paper chromatography test, no trans-isomer was detected within the limit of detection (about ½%) (14 samples tested).

(B) Wet chemical analysis on a typical sample of twice recrystallized product was submitted for analysis of platinum, chlorine and ammonia. The results compared with the NCI specification as follows:

| Elemental Component | Spec. (%) | Analysis (%) |
| --- | --- | --- |
| Platinum | 65.02 ± 0.30 | 65.2 |
| Chlorine | 23.63 ± 0.30 | 23.5 |
| Hydrogen | 2.02 ± 0.30 | 11.1 (as NH$_3$) |
| Nitrogen | 9.3 ± 0.30 | |

(C) The cis-Pt(NH$_3$)$_2$Cl$_2$ was observed to be an orange yellow solid which decomposed at 270° C.

(D) When a sample was refluxed with thiourea in 0.1 N HCl yellow crystals formed which decomposed at 242° C.

(E) IR spectrum run on a Beckman IR-20-X Infrared Spectrometer was compatible with the model spectrum furnished by NCI.

EXAMPLE 7

Experiments were run essentially as described in Step 1 above, in which H$_2$PtCl$_6$ is converted to K$_2$PtCl$_6$, with the following variations:

| Exp. | Reaction Temperature | Yield |
| --- | --- | --- |
| A-7 | 50° C. | 95–98% |
| B-7 | RT | 92–93% |

EXAMPLE 8

A sample of cis-Pt(NH$_3$)$_2$Cl$_2$ was prepared using the method of the present invention essentially as described above in Steps 1 through 6 and then purified three times by the recrystallization from 0.1 N HCl. The sample was sent to an independent laboratory for analyses and it was reported that a HPLC (High Performance Liquid Chromatography) recording showed only peaks for cis-Pt(NH$_3$)$_2$Cl$_2$ and no other peaks. High sensitivity tracings at the region where small peaks for Magnus' green salt and trans-isomer might appear showed no evidence of such impurities in the product.

EXAMPLE 9

Samples of crude cis-Pt(NH$_3$)$_2$Cl$_2$, prepared using the method of the present invention essentially as described above in Steps 1 through 6 and were analyzed for composition:

(1) An IR spectrum run on a Beckman IR-20-X Infrared Spectrometer showed ammine and chloride peaks compatible with the NCI model. An additional unidentified peak was observed at a wavelength of roughly 5.7μ.

(2) In a sample subjected to the NCI paper chromatography test, no trans-isomer was detected within the limit of detection (about ½%).

(3) Several samples were analyzed for silver content, and analysis showed less than 5 ppm silver.

Although the present invention has been described in conjunction with preferred embodiments, it is to be understood that modifications and variations may be resorted to without departing from the spirit and scope of the invention, as those skilled in the art will readily understand. Such modifications and variations are considered to be within the purview and scope of the invention and appended claims.

What is claimed is:

1. A process for preparing cis-$Pt(NH_3)_2Cl_2$ by reacting cis-$[Pt(NH_3)_2(H_2O)_2](NO_3)_2$ with KCl comprising adding KCl rapidly to a solution of cis-$[Pt(NH_3)_2(H_2O)_2](NO_3)_2$ at room temperature, elevating the temperature of the reacting medium to about 70° C. for a period of time sufficient to maximize the reaction, cooling the resultant product while stirring to a temperature no lower then about 10° C., cis-$Pt(NH_3)_2Cl_2$ having precipitated from solution, separating the precipitate from solution substantially immediately.

2. A process for preparing cis-$Pt(NH_3)_2Cl_2$ according to claim 1, wherein the resultant product is cooled to about room temperature.

3. A process for preparing cis-$Pt(NH_3)_2Cl_2$ of high purity and in high yield comprising reacting cis-$Pt(NH_3)_2I_2$ with $AgNO_3$ to form a solution containing cis-$[Pt(NH_3)_2(H_2O)_2](NO_3)_2$ and a AgI precipitate by a method comprising slowly adding the washed and dried cis-$Pt(NH_3)_2I_2$ to an aqueous solution of $AgNO_3$ at room temperature and with rapid stirring, warming the silver-containing mixture to a maximum temperature of about 50° C. and maintaining the temperature of about 50° C. for a period of time sufficient substantially to complete the reaction, then cooling the resultant silver-containing reaction mixture to room temperature and separating the precipitated AgI from the solution containing cis-$[Pt(NH_3)_2(H_2O)_2](NO_3)_2$, treating the solution containing cis-$[Pt(NH_3)_2(H_2O)_2](NO_3)_2$ to precipitate cis-$Pt(NH_3)_2Cl_2$ by addition of MCl, where M=Na or K, by the method comprising adding MCl in stoichiometric excess rapidly to the solution of cis-$[Pt(NH_3)_2(H_2O)_2](NO_3)_2$ at room temperature, elevating the temperature of the cis-$Pt(NH_3)_2Cl_2$-forming mixture to a maximum temperature of about 75° C., maintaining the elevated temperature for a period of time sufficient to maximize formation of cis-$Pt(NH_3)_2Cl_2$, and then cooling the reaction mixture and separating the cis-$Pt(NH_3)_2Cl_2$ precipitate.

4. A process for preparing cis-$Pt(NH_3)_2Cl_2$ according to claim 3, wherein the resultant product is cooled to no lower than about room temperature.

* * * * *